(12) United States Patent
Sharma et al.

(10) Patent No.: US 8,888,285 B2
(45) Date of Patent: Nov. 18, 2014

(54) TUNABLE ACHROMATIZING OPTICAL APPARATUS, METHODS, AND APPLICATIONS

(71) Applicant: University of Rochester, Rochester, NY (US)

(72) Inventors: Robin Sharma, Rochester, NY (US); Yusufu N. Sulai, Milwaukee, WI (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 14/054,962

(22) Filed: Oct. 16, 2013

(65) Prior Publication Data

US 2014/0104572 A1  Apr. 17, 2014

Related U.S. Application Data

(60) Provisional application No. 61/714,459, filed on Oct. 16, 2012.

(51) Int. Cl.
*A61B 3/00* (2006.01)
(52) U.S. Cl.
USPC .......................................... 351/206; 351/246

(58) Field of Classification Search
USPC .................................................. 351/200–246
See application file for complete search history.

(56) References Cited

U.S. PATENT DOCUMENTS

| | | | | |
|---|---|---|---|---|
| 6,315,412 | B1 * | 11/2001 | Snodderly et al. | 351/200 |
| 2008/0080060 | A1 * | 4/2008 | Messerschmidt | 359/654 |
| 2008/0231961 | A1 * | 9/2008 | Meyers | 359/641 |

* cited by examiner

*Primary Examiner* — Mohammed Hasan
(74) *Attorney, Agent, or Firm* — William Greener; Bond, Schoeneck & King, PLLC

(57) ABSTRACT

A tunable, achromatizing optical system for use with a broadband imaging modality system for imaging objects having a range of longitudinal chromatic aberration (LCA) values. The optical system includes an achromatizing component and a parfocal component, for example, a zoom system. A method for tuning the wavefront curvature of different chromatic components of objects having a range of longitudinal chromatic aberration (LCA) values when imaged by a broadband imaging modality system includes the steps of providing a broadband imaging modality system having an entrance pupil, for imaging an object having longitudinal chromatic aberration; providing a tunable, achromatizing optical system; and varying the focal length of the parfocal component while maintaining a conjugate relationship between the achromatizing component and the entrance pupil of the broadband imaging modality system.

13 Claims, 13 Drawing Sheets

TUNABLE ACHROMATIZING OPTICAL APPARATUS, METHODS, AND APPLICATIONS

CROSS-REFERENCE TO RELATED APPLICATIONS

This application claims the benefit of priority under 35 U.S.C. §119(e) to U.S. Provisional Patent Application Ser. No. 61/714,459 filed Oct. 16, 2012, the content of which is incorporated herein by reference in its entirety.

STATEMENT OF GOVERNMENT INTEREST

This work was supported under one or more of the following grants provided by the National Institutes of Health (NIH): EY022371, EY014375 and EY021166.,,,. The U.S. Government has certain rights in this invention.

BACKGROUND

1. Field of the Invention

Embodiments of the invention relate generally to optical systems, methods, and applications. More particularly, embodiments of the invention are directed to a tunable, achromatizing optical system and method, and applications for use in ophthalmic imaging and other optical systems.

2. Technical Background

Adaptive optics based research instruments and the pervasive use of imaging techniques such as optical coherence tomography has made high-resolution ophthalmic imaging of retinal structure at a cellular scale more the clinical norm rather than the exception. Technological advances such as better deformable mirrors, more efficient light sources and detection channels, robust electronic devices, and software engines for controlling equipment in real-time and for post-processing have brought high-resolution retinal imaging into the era of functional imaging. Some of the most attractive and cutting-edge methodologies currently being developed, include AO-enabled optical coherence tomography, hyper-spectral imaging, and two-photon fluorescence imaging all have one thing in common: all of these modalities use broadband light sources. The spectral bandwidth of these sources is in many ways essential to the signal efficiency, resolution, and the clinical efficacy of these instruments. With their development, light sources broader than many tens of nanometers to several hundreds of nanometers in bandwidths will soon be used extensively for high-resolution retinal imaging.

Use of such broadband light sources brings with it certain complexities, notably the inherent chromatic aberration properties of the eye. Longitudinal chromatic aberration (LCA) has been measured and documented over a wavelength regime from 450 to 900 nm. The data for human LCA in the visible regime and in the near infrared regime together inform that the average LCA between 450 and 900 nm is about 1.6 D. In other words, the shortest and longest wavelengths in this band end up focusing roughly 300 nm apart in the retina. While this is the average LCA among the population of people recruited for experiments, the LCA varies from person to person and eye to eye; this variation believed by some to be due to differences in corneal radius.

In vivo two-photon imaging has been demonstrated in the living mouse eye. Ultrashort broadband pulses generated in mode-locked lasers are typically used for two-photon excitation. In terms of diopters (D), the mouse eye suffers from substantial longitudinal chromatic aberration (LCA), which is on average almost an order of magnitude greater than that for the human eye. Depending on the bandwidth of the pulsed laser source, this larger amount of LCA may reduce the efficiency of two-photon excitation by as much as 70% or more.

Achromatizing lenses have previously been designed for the human eye in the visible and infrared regimes to correct for the typical range of the LCA in a given eye, demonstrating improvements in ultrahigh resolution optical coherence tomography. Since the LCA of the eye causes different wavelengths to focus at different retinal layers, an achromatizing lens provides equal and opposite wavefront curvature or dioptric power to all wavelengths across the spectral bandwidth of interest (see e.g., FIG. 1). When the light is focused by the eye, all wavelengths converge to the same layer in the retina. Thus, in ophthalmic systems, an achromatizing lens is typically placed in a conjugate pupil plane of the eye and the magnitude of wavefront curvature would depend on the magnification between the ocular pupil plane and the achromatizing lens. For an AOSLO instrument, for example, the entrance pupil (EP) of the optical system or a plane that is conjugate to the EP, is the most suitable location to place such a lens.

A static achromatizing lens functions as it is designed to for one particular eye whose chromatic aberration profile is equal and opposite to that of the lens. However, given the variability of LCA from eye to eye, the use of a static achromatizing lens provides varying levels of uncorrected LCA in different eyes. For broadband imaging modalities, uncorrected LCA can result in different wavelengths being focused too far away from each other. For optical coherence tomography, this will adversely affect the axial resolution of the instrument. For hyperspectral imaging, which relies on capturing the contrast of the tissue at different wavelengths, the lack of reliability of imaging the same layer at different wavelengths is detrimental to the clinical information this modality can convey. For two-photon imaging, depending on the pulse-width of light used the uncorrected LCA can result in spatio-temporal focusing discrepancies that have the potential to decimate the efficiency of two photon fluorescence as well as spatial resolution.

In view of the aforementioned shortcomings known in the art and the challenges presented by uncorrected LCA, it would be advantageous to have a tunable LCA-correcting optical system operable over a spectral range from about 400 nm to about 1000 nm.

SUMMARY OF THE INVENTION

As may be used herein for purposes of the present disclosure, the term 'about' means the amount of the specified quantity plus/minus a fractional amount thereof that a person skilled in the art would recognize as typical and reasonable for that particular quantity or measurement; for example, 'about 1000 nm' may mean 980, 981, 982 ... 1001, 1002 ... 1020 nm. Likewise, the term 'substantially' means as close to or similar to the specified term being modified as a person skilled in the art would recognize as typical and reasonable.

The term 'controller' as may be used herein is used generally to describe various apparatus relating to the operation of one or more light sources. A controller can be implemented in numerous ways (e.g., such as with dedicated hardware) to perform various functions discussed herein. A 'processor' is one example of a controller which employs one or more microprocessors that may be programmed using software (e.g., microcode) to perform various functions. A controller may be implemented with or without employing a processor, and also may be implemented as a combination of dedicated hardware to perform some functions and a processor (e.g., one or more programmed microprocessors and associated circuitry) to perform other functions. Examples of controller components include, but are not limited to, conventional microprocessors, application specific integrated circuits (ASICs), and field-programmable gate arrays (FPGAs).

In various implementations, a processor or controller may be associated with one or more storage media (generically referred to as 'memory,' e.g., volatile and non-volatile computer memory such as RAM, PROM, EPROM, and EEPROM, floppy disks, compact disks, optical disks, magnetic tape, etc.). The storage media may be encoded with one or more programs that, when executed on one or more processors and/or controllers, perform certain functions. Various storage media may be fixed within a processor or controller or may be transportable, such that the one or more programs stored thereon can be loaded into a processor or controller so as to implement various aspects of the invention. The terms 'program' or 'computer program' as may be used herein refer in a generic sense to any type of computer code (e.g., software or microcode) that can be employed to program one or more processors or controllers.

The term 'network' as may be used herein as used herein refers to any interconnection of two or more devices (including controllers or processors) that facilitates the transport of information (e.g. for device control, data storage, data exchange, etc.) between any two or more devices and/or among multiple devices coupled to the network. As should be readily appreciated, various implementations of networks suitable for interconnecting multiple devices may include any of a variety of network topologies and employ any of a variety of communication protocols. Additionally, any one connection between two devices may represent a dedicated connection between the two systems, or alternatively a non-dedicated connection. In addition to carrying information intended for the two devices, such a non-dedicated connection may carry information not necessarily intended for either of the two devices (e.g., an open network connection). Furthermore, it should be readily appreciated that various networks of devices may employ one or more wireless, wire/cable, and/or fiber optic links to facilitate information transport throughout the network.

The term 'user interface' as may be used herein refers to an interface between a human user or operator and one or more devices that enables communication between the user and the device(s). Examples of user interfaces include, but are not limited to, switches, potentiometers, buttons, dials, sliders, a mouse, keyboard, keypad, various types of game controllers (e.g., joysticks), track balls, display screens, various types of graphical user interfaces (GUIs), touch screens, microphones and other types of sensors that may receive some form of human-generated stimulus and generate a signal in response thereto.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

An embodiment of the invention is a tunable, achromatizing optical system for use with a broadband imaging modality system for imaging objects having a range of longitudinal chromatic aberration (LCA) values, noting that LCA is conventionally described in graphical terms as the plot of axial focal length as a function of wavelength or as a plot of wavefront curvature in diopters as a function of wavelength. The magnitude of LCA is always defined over a spectral range and is quantified as the difference in focal lengths or difference in dioptric curvature between the shortest and longest wavelength in the spectral range. Since the plots of LCA over a spectral range are not linear, variations in LCA from subject to subject can be quantified as a distribution of difference in focal lengths or curvatures (in diopters). Graphically this shows up as different scaled versions of the base LCA curve. Thus, the range of LCA values referred to herein are a range of curves that are scaled versions of each other. As the scaling parameter changes, the LCA curve changes and the absolute difference between the shortest and longest wavelengths changes. The embodied optical system includes an achromatizing component and a parfocal component disposed on an object side of the achromatizing component and in optical alignment therewith, wherein the parfocal component has a first image-side optic and a last object-side optic, further wherein the achromatizing component is disposed one focal length of the first image-side optic from the first image-side optic. According to various exemplary, non-limiting aspects and versions of embodiments, the tunable, achromatizing optical system may additionally include the following features or characteristics;

wherein the object to be imaged is an in-vivo eye;
wherein the achromatizing component is achromatizing over the wavelength range from about 400 nanometers (nm) to about 1000 nm;
   wherein the achromatizing component is achromatizing over the wavelength range from about 400 nanometers (nm) to about 900 nm;
wherein the tunable, achromatizing optical system is 'pupil-matched' to the optical system with respect to its use with the broadband imaging modality system for imaging objects having a range of LCA values;
wherein the achromatizing component comprises one or more optical lenses or any other optical component that can provide different wavefront curvatures to different wavelengths;
wherein the parfocal component is a zoom lens;
   wherein the tunable, achromatizing optical system is adapted for a mouse eye, wherein the zoom lens has a zoom range that is equal to or greater than 1.73:1 for an input beam size of 6.2 mm diameter, an entrance pupil diameter of 5 mm, and an ocular pupil diameter of the dilated mouse eye equal to about 2 mm;
   wherein the tunable, achromatizing optical system is adapted for a human eye, wherein the zoom lens has a zoom range that is equal to or greater than 1.06:1 for an input beam size of 7.5 mm diameter, an entrance pupil diameter of 7.5 mm, and an ocular pupil diameter of the dilated human eye equal to about 7.5 mm; —wherein the tunable, achromatizing optical system comprises a refractive zoom lens and refractive achromatizing lens;
   wherein the tunable, achromatizing optical system comprises a reflective zoom lens and refractive achromatizing lens
   wherein the tunable, achromatizing optical system comprises a catadioptric zoom lens and refractive achromatizing lens.

An embodiment of the invention is a method for tuning the wavefront curvature of different chromatic components of objects having a range of longitudinal chromatic aberration (LCA) values when imaged by a broadband imaging modality system. The method includes the steps of providing a broadband imaging modality system for imaging an object having longitudinal chromatic aberration, wherein the broadband imaging modality system has an entrance pupil; providing a tunable, achromatizing optical system as set forth hereinabove; positioning the tunable, achromatizing optical system one focal length from the entrance pupil of the broadband imaging modality system; varying the focal length of the parfocal component while maintaining a conjugate relationship between the achromatizing component and the entrance pupil of the broadband imaging modality system. According to various exemplary, non-limiting aspects and versions of embodiments, the method may additionally include the following features, steps, or characteristics:

wherein providing a broadband imaging modality system further comprises providing an adaptive optics scanning laser ophthalmoscope (AOSLO).

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention, and together with the description serve to explain the principles and operation of the invention.

DETAILED DESCRIPTION OF NON-LIMITING, EXEMPLARY EMBODIMENTS

Reference will now be made in detail to the present exemplary embodiments of the invention, examples of which are illustrated in the accompanying drawings. Wherever possible, the same reference numbers will be used throughout the drawings to refer to the same or like parts.

Figure 2:
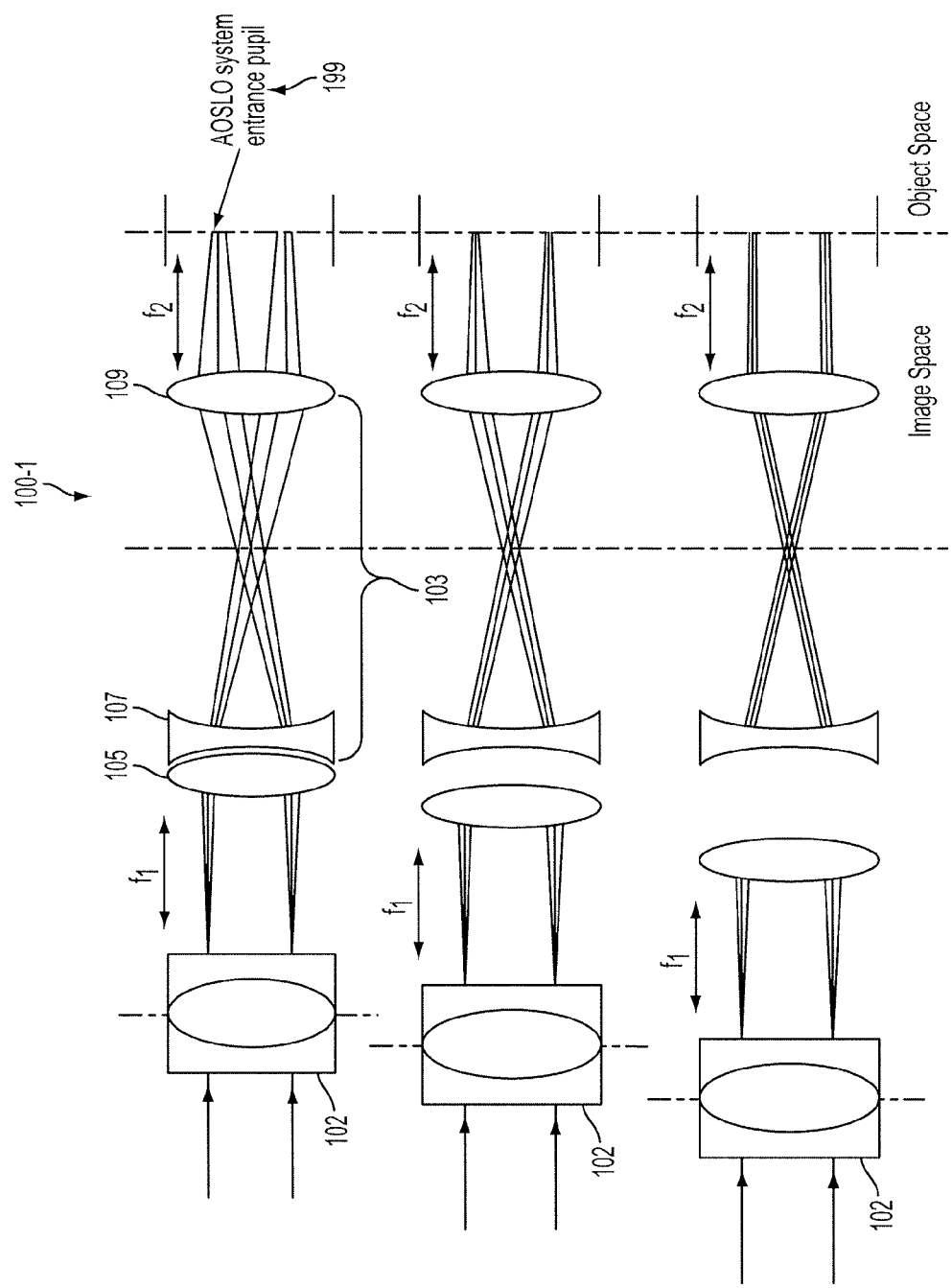
FIG. 2 schematically illustrates a tunable, achromatizing optical system including a refractive achromatizing component and a refractive parfocal component, in three tuning ranges, according to an illustrative embodiment of the invention.

FIG. 2 schematically illustrates a tunable, achromatizing optical system 100-1 including a refractive achromatizing component 102 and a refractive parfocal component 103, in three tuning ranges from the top to the bottom of the drawing page. The illustrated refractive achromatizing component 102 is in the form of a triplet lens that is well known in the art, and the refractive parfocal component 103 is in the form of a zoom lens comprising a first image side lens 105 having a focal length $f_1$, an intermediate lens 107, and a first object side lens 109 having a focal length $f_2$.

Figure 1:
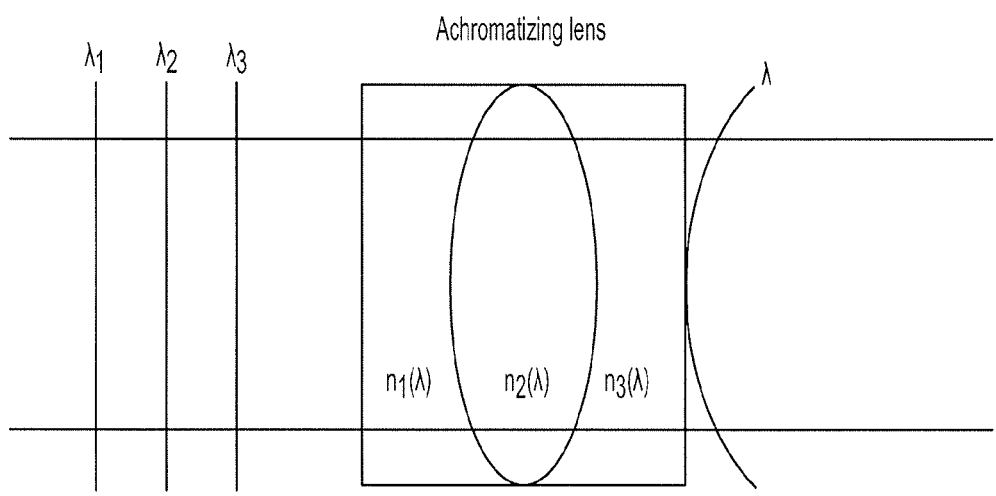
FIG. 1 is a schematic diagram illustrating the operation of a static achromatizing lens.

The achromatizing lens 102 provides wavefront curvatures to each wavelength component of a broadband light source (as illustrated in FIG. 1), which are equal and opposite to the LCA of the eye being measured/imaged (not shown). The achromatizing lens 102 is disposed in a plane that is optically conjugate to the pupil of the eye, and for an AOSLO instrument as disclosed by example herein, the entrance pupil (EP) 199 of the AOSLO optical system (or in a plane that is conjugate to the EP, as shown) is the most suitable location to place the lens.

The zoom lens 103 is used for tuning the wavefront curvature of the different chromatic components. In a prototype embodiment, a static achromatizing lens (102) designed for collimated light with respect to the chromatic mouse model eye was developed in ray-tracing software. This element is then relayed to EP 199 of the ASOLO imaging system using a 4-f telescope 103 by placing it one focal length, $f_1$, away from the first lens 105 of the telescope, where $f_1$ is the combined focal length of the doublet (105, 107) (which depends on the focal length of the individual lenses and their separation). The EP 199 is therefore located one focal length, $f_2$, after the first object side lens 109 having a focal length $f_2$.

As illustrated in the three modalities of FIG. 2, to compensate for different values of LCA the focal length of one (105) of the two (105, 107) elements of the telescope 103 are varied. While maintaining the required conjugate relationship between the static achromatizing element 102 and the EP 199, varying the focal lengths of one of the elements scales the wavefront curvatures of different wavelengths at the EP 199, providing a tunable chromatic correction. In the illustrated optical system, lens element 105, 107 form an air-spaced doublet as one element of the telescope; thus adjusting the spacing between the constituents of the doublet will change the focal length and thereby provide the necessary tuning for chromatic correction. Design of the zoom lens system was performed in ray-tracing software and the system's feasibility was verified. The tuning range of the illustrated zoom system was sufficient to provide chromatic correction for the range over which the LCA was expected to vary in the mouse eye. Similarly, the tuning range of a zoom system was also established for providing chromatic correction for the range over which the LCA is expected to vary in the human eye.

LCA variation plots of different eyes, plotted with respect to a reference wavelength, are nearly scaled versions of each other. This implies that a tunable achromatizing lens must be capable of scaling the wavefront curvature at different wavelengths with respect to a reference wavelength.

We have presented a novel, tunable achromatizing optical system that comprises the optical combination of an achromatizing component and a parfocal component, wherein the achromatizing component is maintained at the front focal plane of the parfocal component and the entrance pupil of the ophthalmic imaging system (not part of the invention per se) is maintained at the back focal plane of the parfocal component.

It will be appreciated that parfocal systems such as the zoom lens system disclosed herein can take a variety of optical forms; e.g., refractive, reflective, and catadioptric zoom lens systems. Various approaches could be utilized in conjunction to tune the achromatizing correction for the eye. They can broadly be classified into the following categories:

1) Refractive zoom lens and refractive achromatizing lens: A telescope comprised of refractive elements, whose separation with respect to each other changes in a pre-determined manner. The track of one element with respect to another would be maintained in such a way as to ensure that the achromatizing lens is always at the front focal plane of the telescope and the entrance pupil of the ophthalmic system is always maintained at the back focal plane of the telescope.

2) Reflective zoom lens and refractive achromatizing lens: A telescope comprised entirely of reflective components such as spherical or conical surfaces whose separation with respect to each other changes in a pre-determined manner. The track of one element with respect to another would be maintained in such a way as to ensure that the achromatizing lens is always at the front focal plane of the telescope and the entrance pupil of the ophthalmic system is always maintained at the back focal plane of the telescope. This is a particularly advantageous implementation because the use of reflective elements reduces unnecessary dispersion and chromatic aberration that can be of concern in, e.g., a two-photon imaging system when refractive components are deployed for the zoom telescope.

3) Catadioptric zoom lens and refractive achromatizing lens: A telescope comprised of reflective and refractive elements, whose separation with respect to each other changes in a pre-determined manner. The track of one element with respect to another would be maintained in such a way as to ensure that the achromatizing lens is always at the front focal plane of the telescope and the entrance pupil of the ophthalmic system is always maintained at the back focal plane of the telescope.

Figure 3:
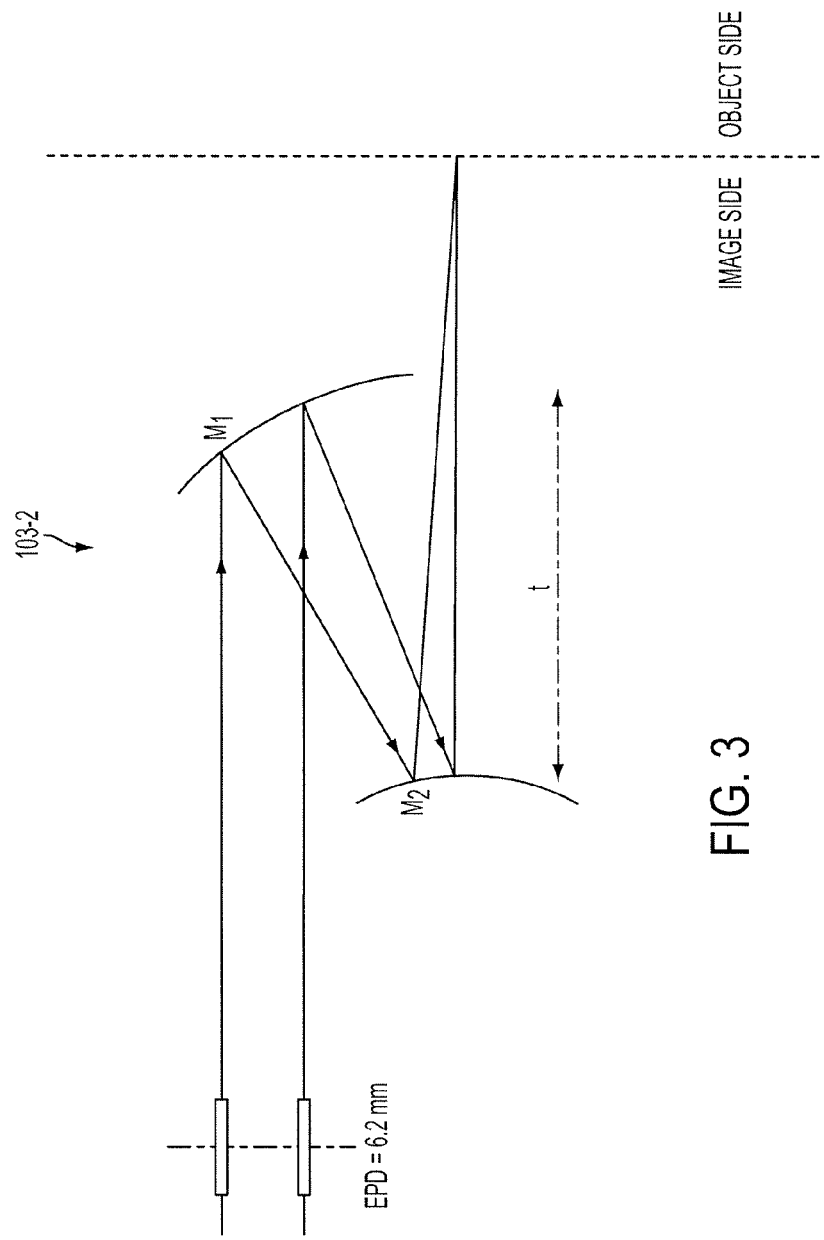
FIG. 3 schematically illustrates an image-side, variable focal length portion of a reflective parfocal component in the form of a decentered Cassegrain telescope in one focusing modality, according to an illustrative aspect of the invention.
Figure 4:
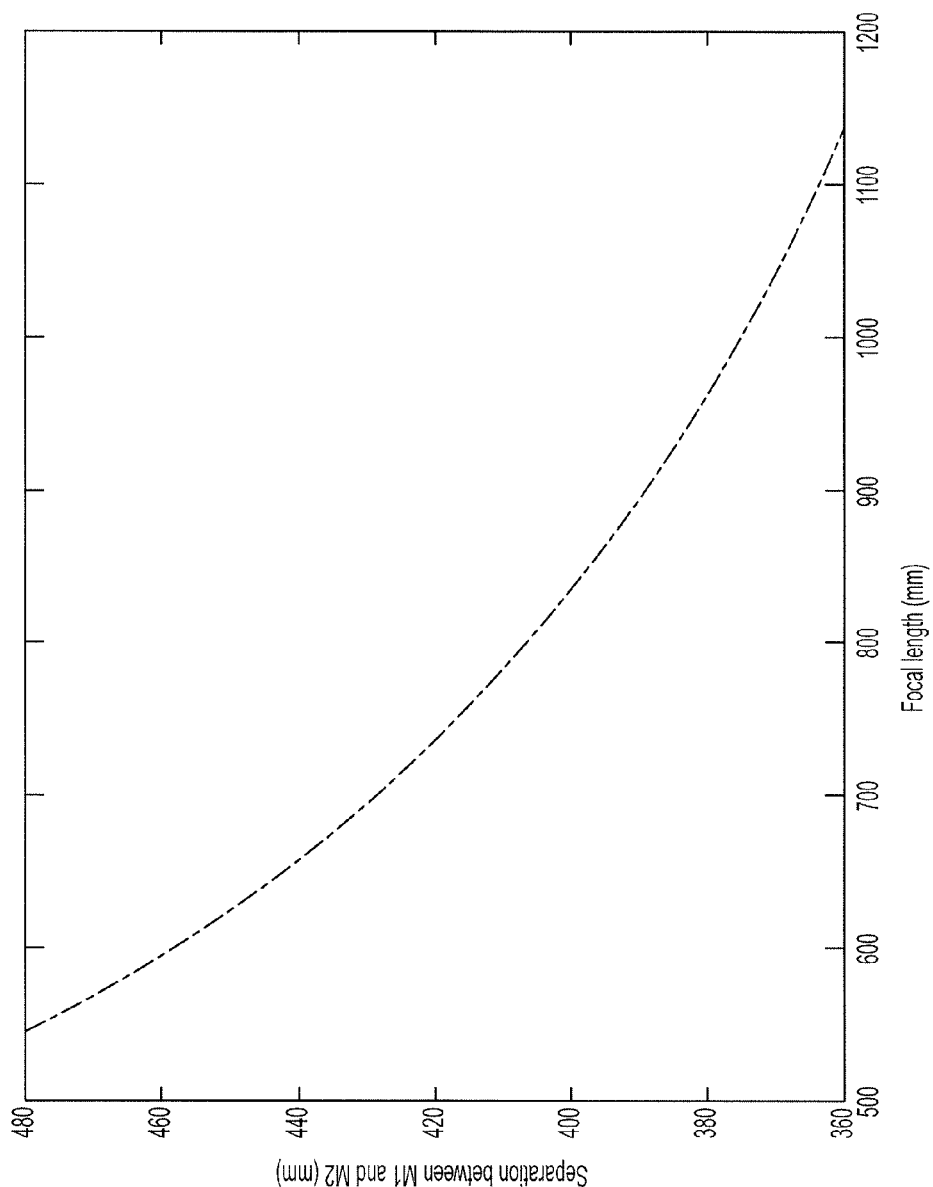
FIG. 4 graphically shows the variation in separation of the primary and secondary mirrors of the telescope shown in FIG. 3 as a function of focal length, according to an illustrative aspect of the invention.

FIG. 3 schematically illustrates an image-side, variable focal length portion of a reflective parfocal component 103-2 in the form of a decentered Cassegrain telescope in one focusing modality, where the variable separation distance between primary mirror, M1, and secondary mirror, M2, is represented by t. The graph in FIG. 4 illustrates how t changes as a function of focal length of the zoom system.

Figure 5:
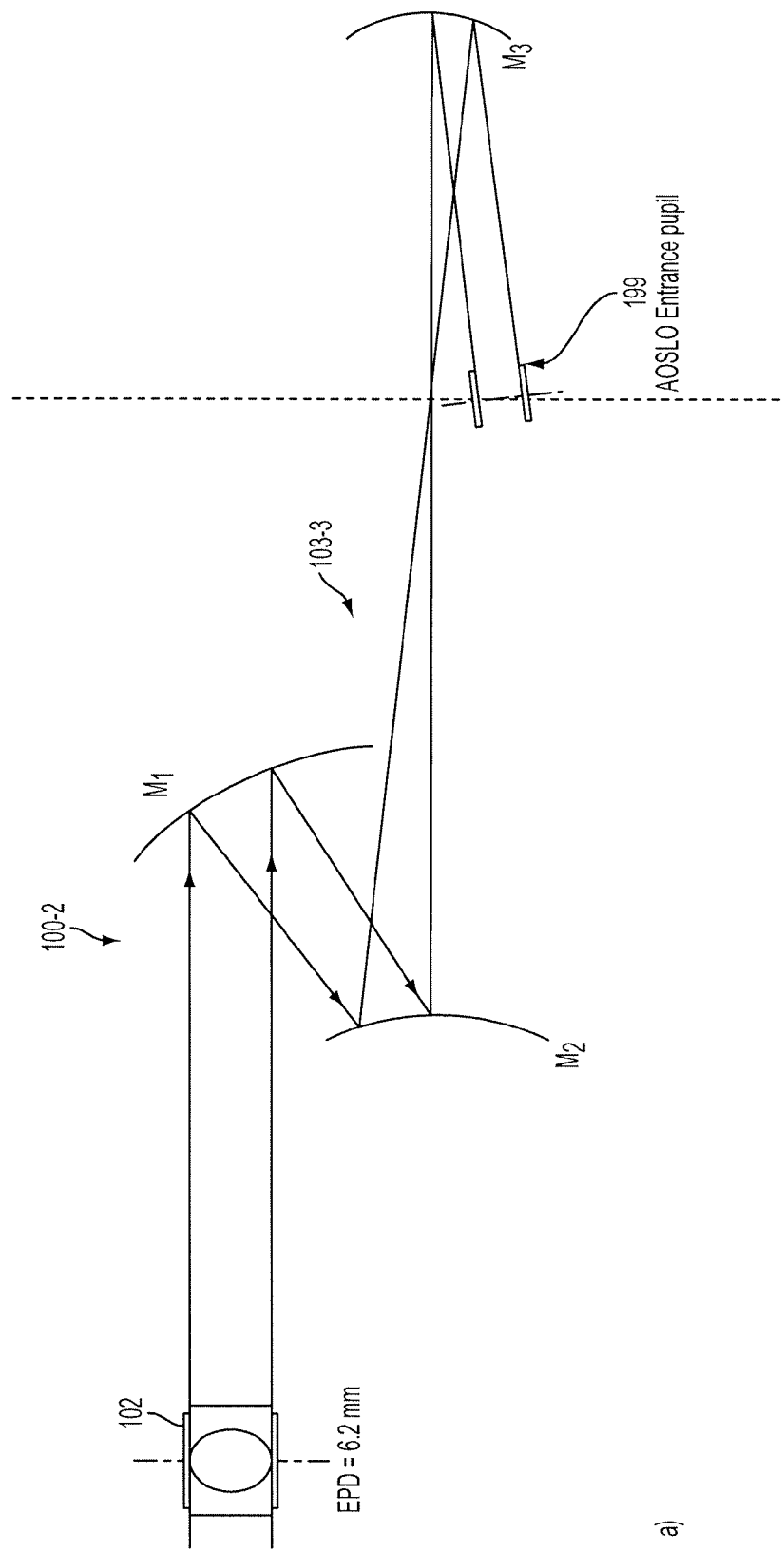
FIG. 5(a, b, c) schematically illustrate the decentered Cassegrain telescope in three different focusing modalities while maintaining the conjugate relationship between the achromatizing component and the entrance pupil of the AOSLO imaging optical system, according to an illustrative aspect of the invention.
Figure 5:
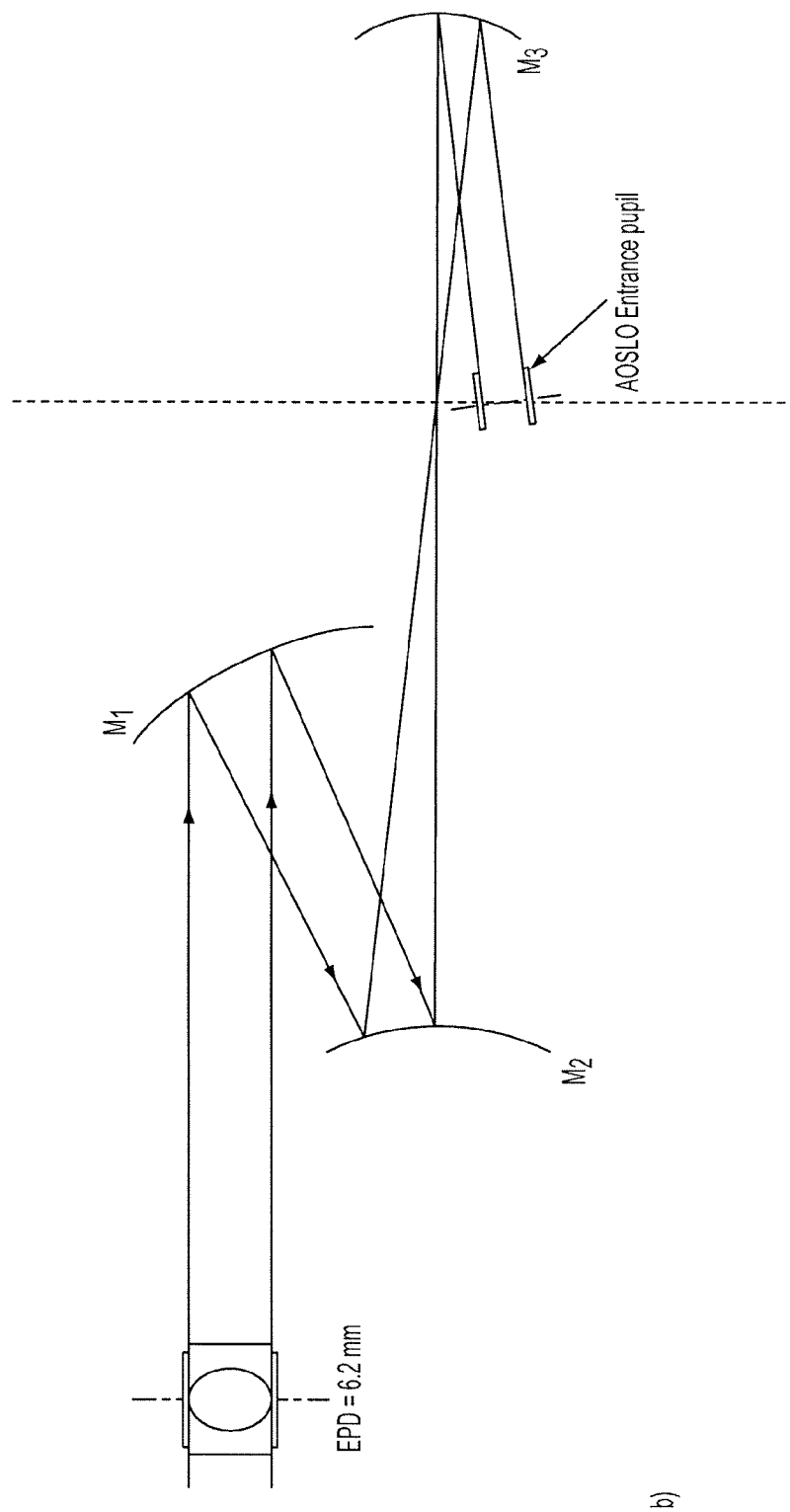
Figure 5:
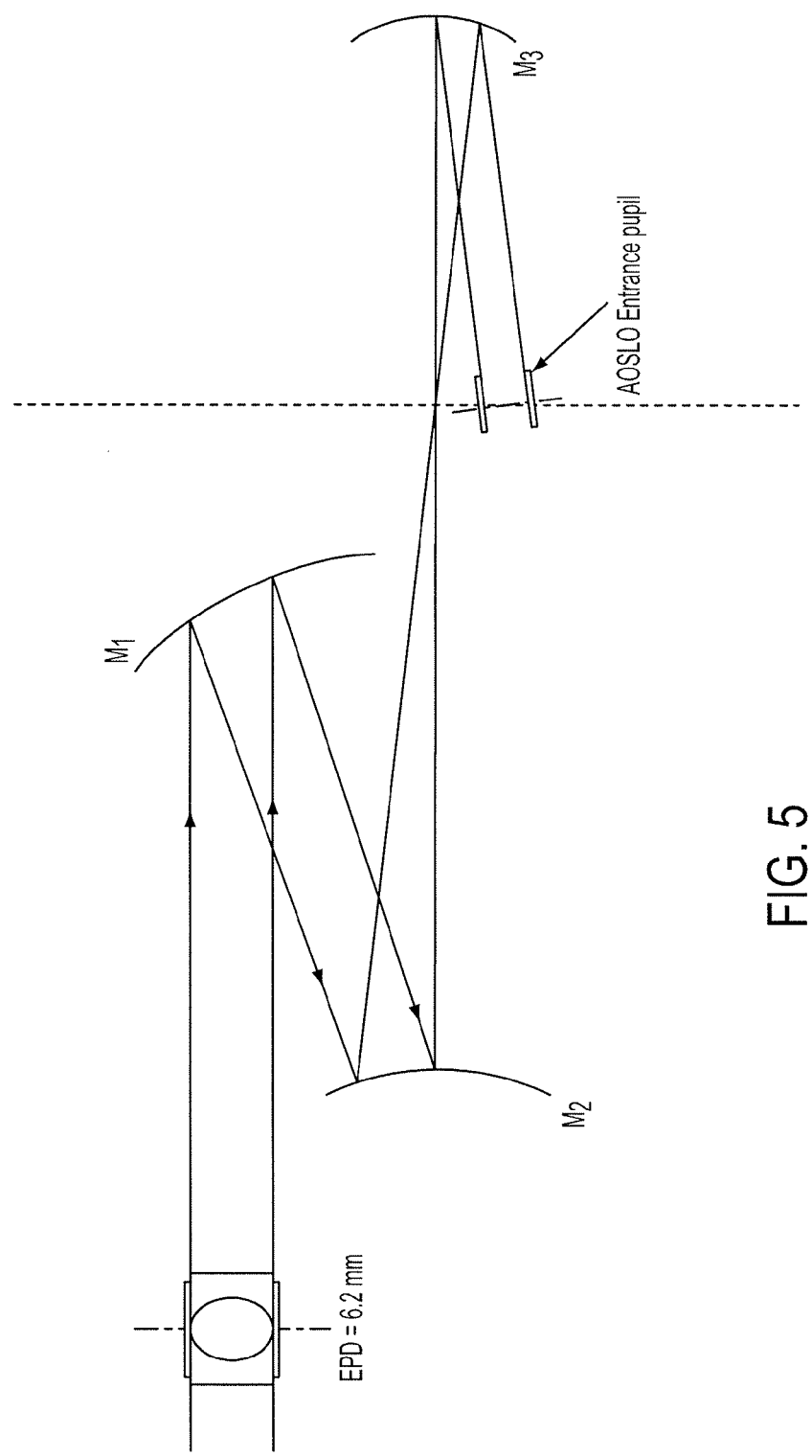

FIG. 5(a, b, c) schematically illustrate a tunable, achromatizing optical system 100-2 including a refractive achromatizing component 102 and an optically aligned, decentered Cassegrain telescope 103-3 in three respectively different focusing modalities while maintaining the necessary conjugate relationship between the achromatizing component 102 and the entrance pupil 199 of an AOSLO imaging optical system (not shown).

Figure 6:
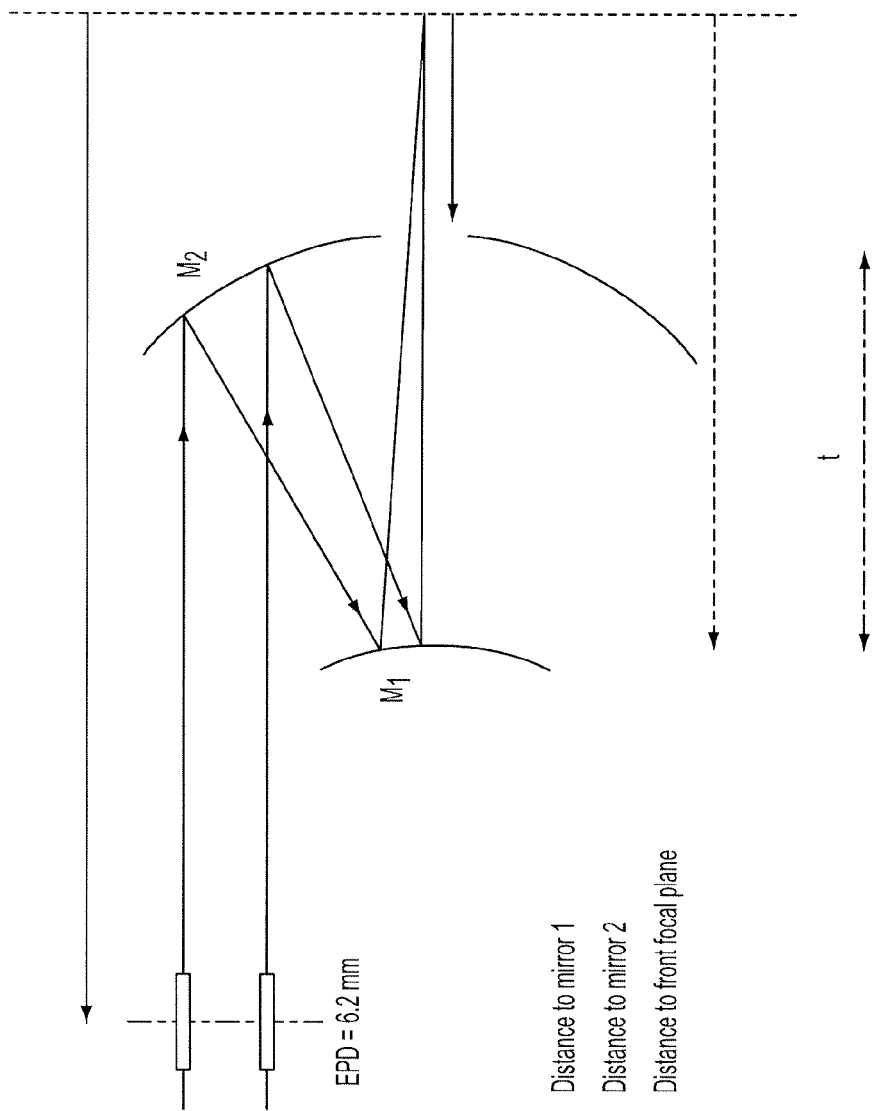
FIG. 6 schematically illustrates distances in an image-side portion of a reflective parfocal component, according to an illustrative aspect of the invention.

FIG. 6 schematically illustrates distances in an image-side portion of a reflective parfocal component, from an entrance pupil of the achromatizing component for an input beam size of 6.2 mm diameter to mirror M1, mirror M2, and to the front focal plane of the system, where t is the variable separation distance between mirrors M1 and M2.

Figure 7:
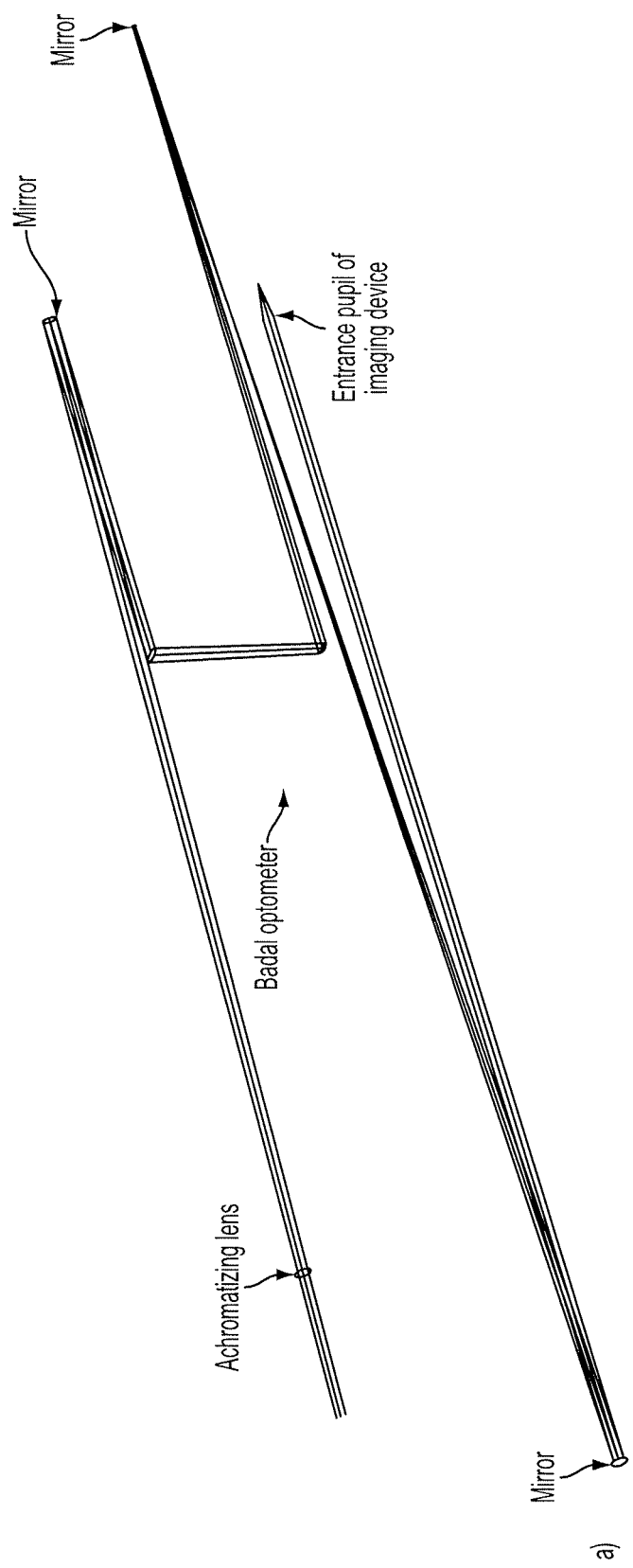
FIG. 7(a, b, c) diagrammatically show light paths for three focusing modalities of a tunable, achromatizing optical system, according to illustrative aspects of the invention.
Figure 7:
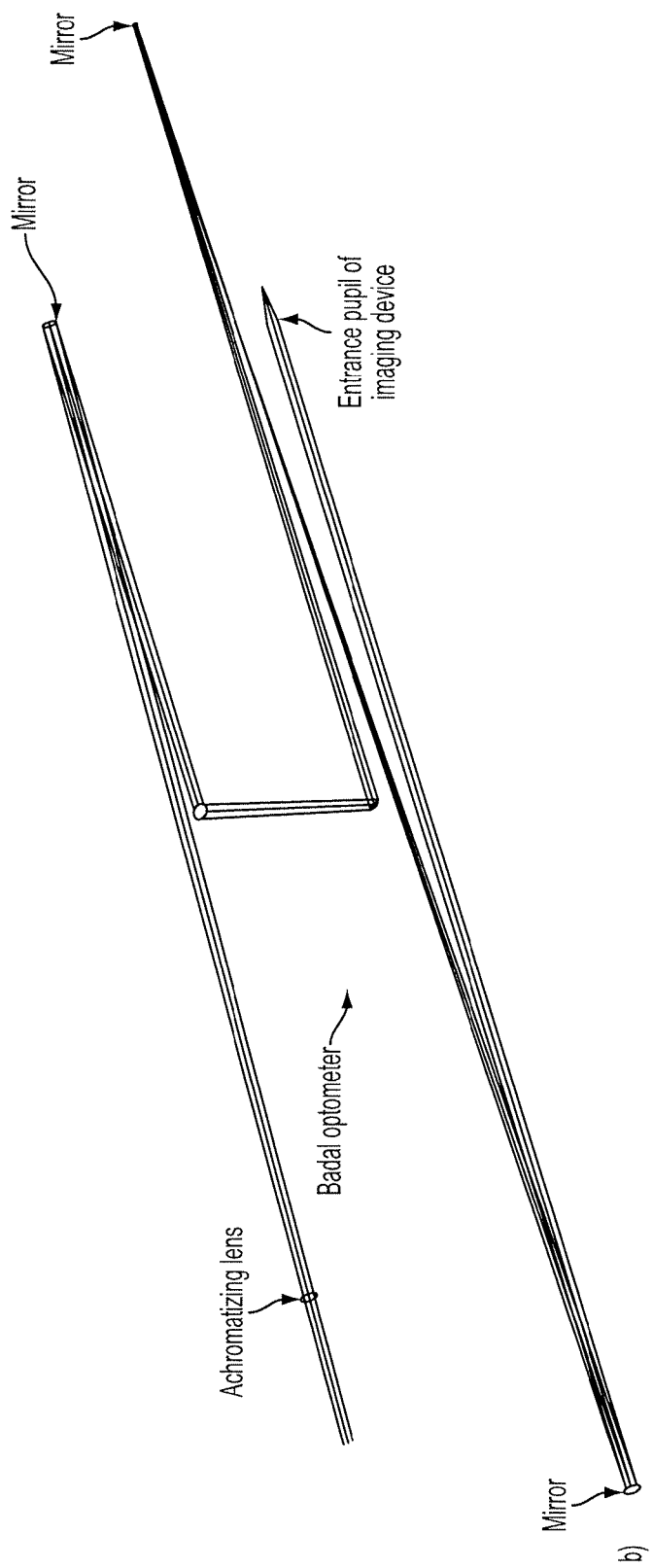
Figure 7:
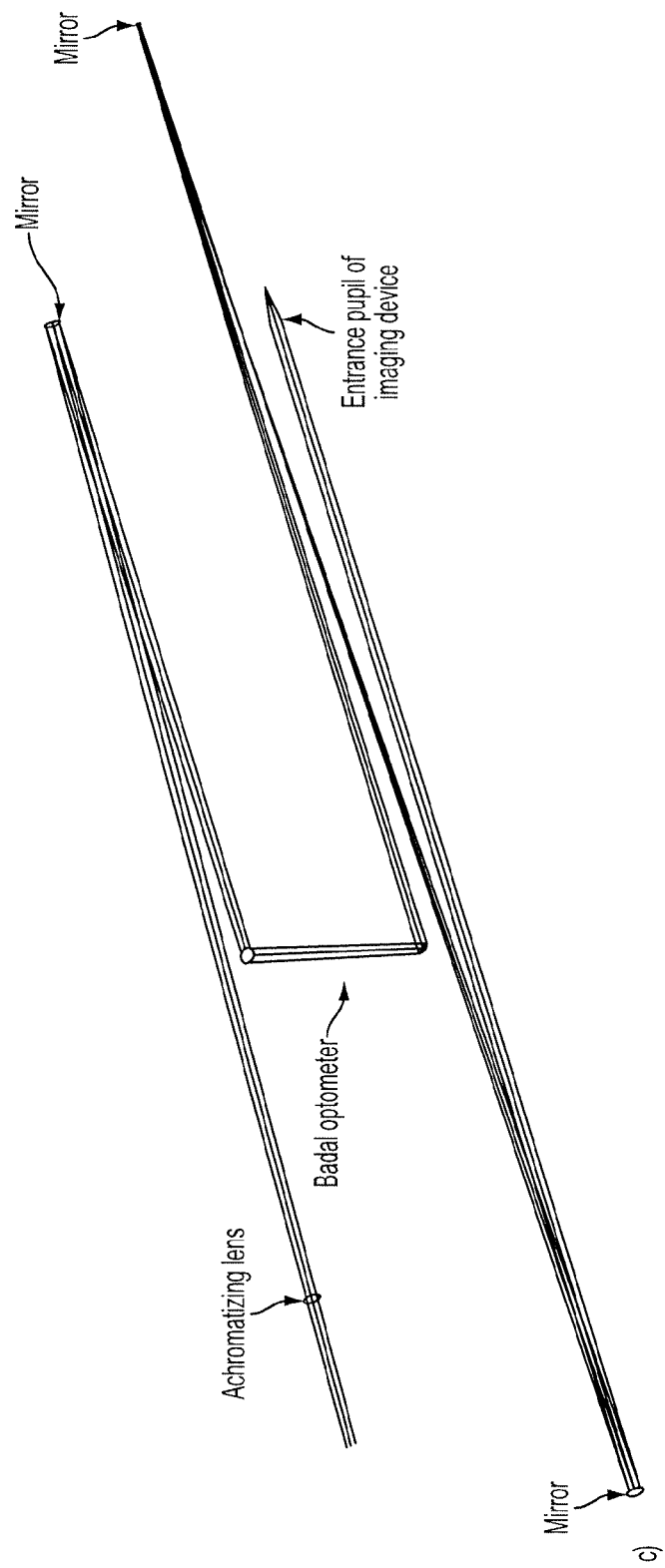

FIG. 7(a, b, c) diagrammatically show light paths for three respective focusing modalities of a tunable, achromatizing optical system, according to illustrative aspects of the invention. These designs are best described as off-axis spherical mirror-based multi-element telescopes or variations on a Gregorian telescope system. The separation between the first two elements is changed to tune the achromatizing properties of the device. A Badal optometer is introduced between those two elements to change the separation between them. The achromatizing lens is moved in such a way that it is always maintained at the front pupil of the telescope and the back pupil plane of the telescope is pupil-matched with the entrance pupil of the ophthalmic system to ensure that any modification in wavefront curvature introduced by the zoom system is faithfully reproduced at the ocular pupil plane of the ophthalmic system.

Figure 8:
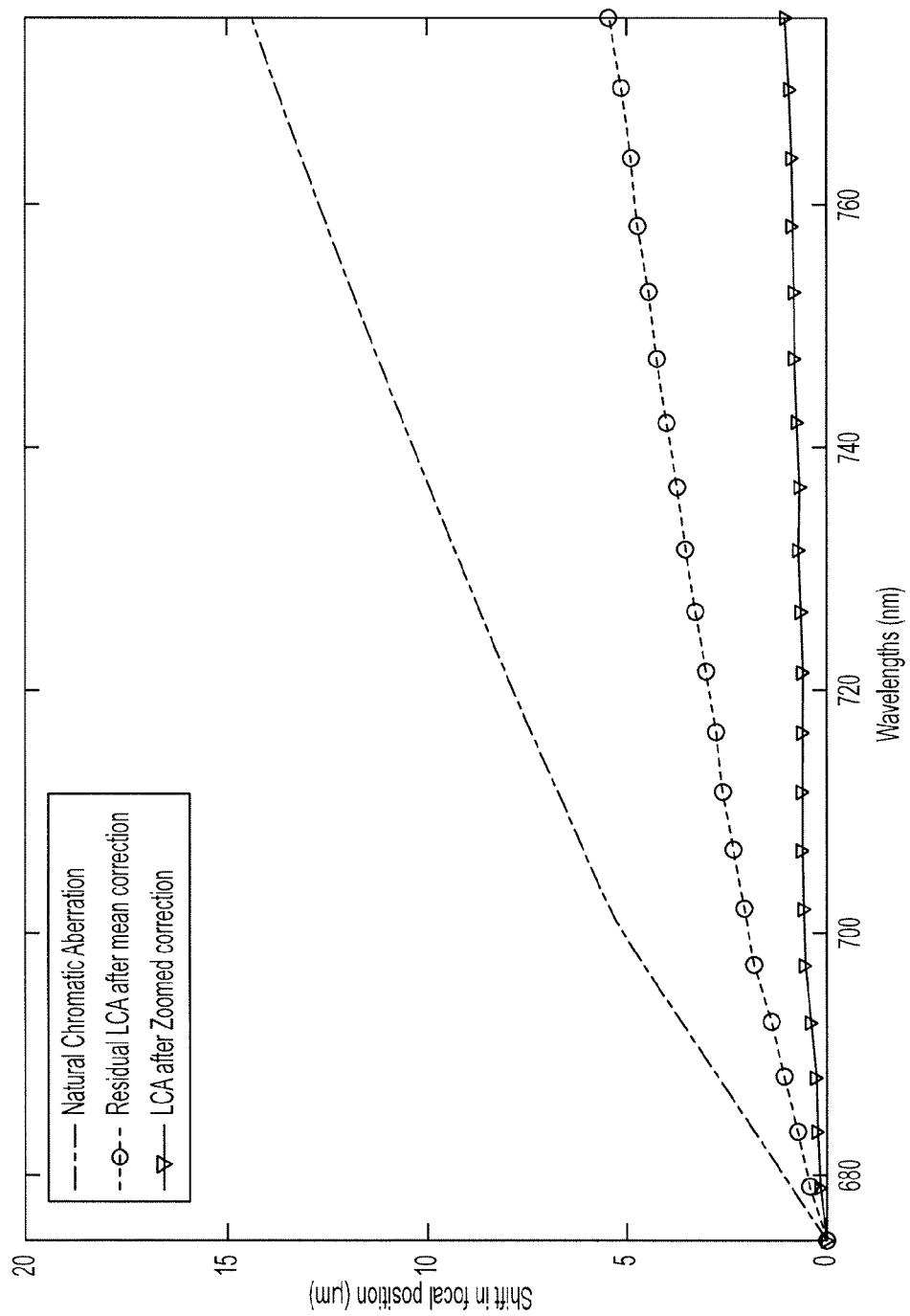
FIG. 8 graphically shows experimental results for correcting LCA in a mouse eye using a system as embodied herein.

FIG. 8 graphically shows the simulated results for correcting LCA in a mouse eye using a system as embodied herein. The dashed line curve illustrates the natural chromatic aberration of a mouse eye at one extreme condition over the labeled wavelengths; the circled line shows the residual LCA after mean correction; and the inverted triangle line shows the resulting tuned, corrected LCA for this extreme case.

Figure 9:
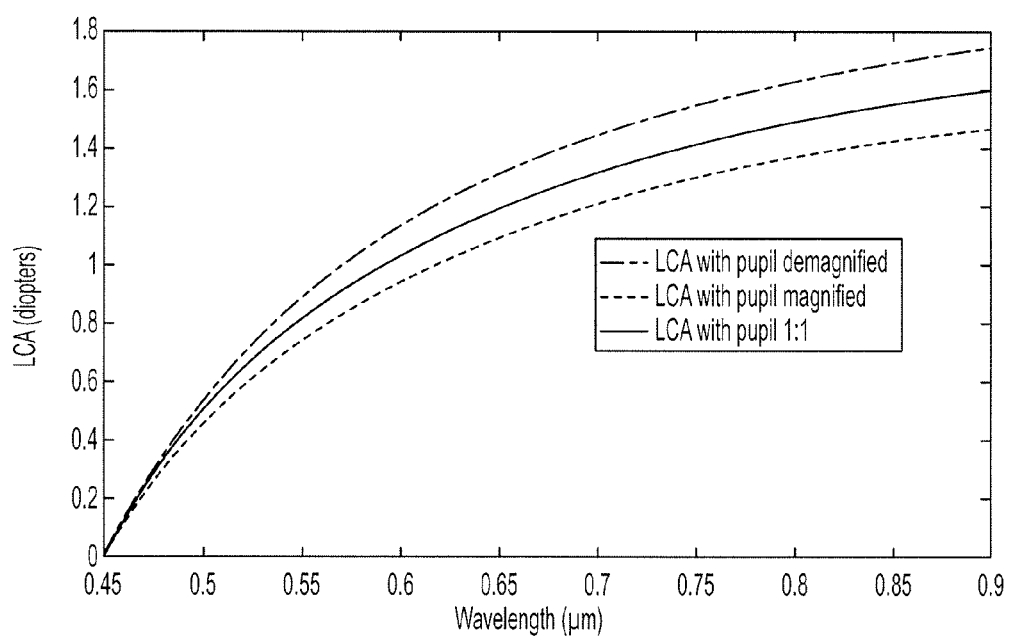
FIG. 9 is a graph of plots showing the impact of zooming the tunable achromatizing lens, according to an illustrative aspect of the invention.

In FIG. 9, the curves show the impact of zooming the tunable achromatizing lens when parameters are defined for the human eye. When the zoom lens is at a 1:1 magnification, the achromatizing lens is imaged directly to the entrance pupil of the system and it corrects the native LCA of about 1.6 D between 450 and 900 nm. As the system is zoomed, the magnification between the achromatizing lens and the entrance pupil of the system changes and the LCA correction applied changes with it. At one extreme when the pupil is demagnified the system goes on to correct the native LCA of 1.75 D and, at the other extreme when the pupil is magnified, LCA of about 1.5 D is corrected. This provides sufficient range to correct for the estimated LCA variability expected from corneal curvature variations among people.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

We claim:

1. A tunable, achromatizing optical system for use with a broadband imaging modality system for imaging objects having a range of longitudinal chromatic aberration (LCA) values, comprising:
   an achromatizing component; and
   a parfocal component disposed on an object side of the achromatizing component and in optical alignment therewith,
   wherein the parfocal component has a first image-side optic and a last object-side optic, further wherein the achromatizing component is disposed at a front focal plane of the parfocal component.

2. The tunable, achromatizing optical system of claim 1, wherein the achromatizing component is achromatizing over the wavelength range from 450 nanometers (nm) to 900 nm.

3. The tunable, achromatizing optical system of claim 1, wherein the tunable, achromatizing optical system is a 'pupil-matching' optical system with respect to its use with the broadband imaging modality system for imaging objects having a range of LCA values.

4. The tunable, achromatizing optical system of claim 1, wherein the achromatizing component comprises one or more optical lenses.

5. The tunable, achromatizing optical system of claim 1, wherein the parfocal component is a zoom lens.

6. The tunable, achromatizing optical system of claim 1, wherein the object to be imaged is an in-vivo eye.

7. The tunable, achromatizing optical system of claim 5, comprising a refractive zoom lens and refractive achromatizing lens.

8. The tunable, achromatizing optical system of claim 5, comprising a reflective zoom lens and refractive achromatizing lens.

9. The tunable, achromatizing optical system of claim 8, wherein the reflective zoom lens comprises a Cassegrain telescope.

10. The tunable, achromatizing optical system of claim 9, wherein the reflective zoom lens comprises a decentered Cassegrain telescope.

11. The tunable, achromatizing optical system of claim 5, comprising a catadioptric zoom lens and refractive achromatizing lens.

12. A method for tuning the wavefront curvature of different chromatic components of objects having a range of longitudinal chromatic aberration (LCA) values when imaged by a broadband imaging modality system, comprising:
   providing a broadband imaging modality system for imaging an object having longitudinal chromatic aberration, wherein the broadband imaging modality system has an entrance pupil;
   providing a tunable, achromatizing optical system as set forth in claim 3;
   positioning the tunable, achromatizing optical system one focal length from the entrance pupil of the broadband imaging modality system;
   varying the focal length of the parfocal component while maintaining a conjugate relationship between the achromatizing component and the entrance pupil of the broadband imaging modality system.

13. The method of claim 12, wherein providing a broadband imaging modality system further comprises providing an adaptive optics scanning laser ophthalmoscope (AOSLO).

* * * * *